United States Patent
Smith et al.

(10) Patent No.: US 9,248,085 B2
(45) Date of Patent: Feb. 2, 2016

(54) EFFECTIVE DEPILATORY ARTICLE

(75) Inventors: Paul James Smith, Whitton (GB);
Graeme William Watts, Woking (GB);
Coralie Claude Monique Rowe,
Chertsey (GB); Sarah Jayne Campbell,
Canterbury (GB); Neil Charles Dring,
Medmenham (GB); Paul Albert Sagel,
Maineville, OH (US); **Rajeev Kumar
Passi, West Chester, OH (US); Shekhar
Mitra, Cincinnati, OH (US); Norman
Scott Broyles**, Hamilton, OH (US)

(73) Assignee: The Procter & Gamble Company,
Cincinnati, OH (US)

( * ) Notice: Subject to any disclaimer, the term of this patent is extended or adjusted under 35 U.S.C. 154(b) by 0 days.

(21) Appl. No.: 13/588,326

(22) Filed: Aug. 17, 2012

(65) Prior Publication Data

US 2013/0042418 A1     Feb. 21, 2013

Related U.S. Application Data

(60) Provisional application No. 61/524,360, filed on Aug. 17, 2011.

(51) Int. Cl.
*A61Q 9/04*     (2006.01)
*A61K 8/46*     (2006.01)
*A61K 8/21*     (2006.01)

(52) U.S. Cl.
CPC ... *A61K 8/46* (2013.01); *A61K 8/21* (2013.01); *A61Q 9/04* (2013.01)

(58) Field of Classification Search
CPC .............. A61K 8/21; A61K 8/46; A61Q 9/04
USPC .................... 424/78.03, 70.1; 8/94.15, 94.16
See application file for complete search history.

(56) References Cited

U.S. PATENT DOCUMENTS

| | | | |
|---|---|---|---|
| 2,202,829 A | 6/1940 | Buff | |
| 2,954,324 A | 9/1960 | Brummer | |
| 3,808,637 A | 5/1974 | Lapidus | |
| 4,282,877 A | 8/1981 | Mathews | |
| 4,314,572 A * | 2/1982 | de la Guardia et al. | 132/204 |
| 4,401,663 A | 8/1983 | Buckwalter et al. | |
| 4,424,205 A | 1/1984 | LaHann et al. | |
| 4,830,633 A * | 5/1989 | Hori et al. | 8/160 |
| 6,336,462 B1 | 1/2002 | Santelli et al. | |
| 7,404,967 B2 * | 7/2008 | Hahn et al. | 424/401 |

(Continued)

FOREIGN PATENT DOCUMENTS

| | | | | |
|---|---|---|---|---|
| AU | WO 2008034178 A1 * | 3/2008 | | A61K 8/347 |
| CA | 2354929 A1 | 2/2002 | | |

(Continued)

OTHER PUBLICATIONS

"Cool Gel Cooling Hair Removal Gel"; Record ID 1519084; Church & Dwight, 3 pages; GNPD; MINTEL.

(Continued)

*Primary Examiner* — Vasu Jagannathan
*Assistant Examiner* — Preeti Kumar
(74) *Attorney, Agent, or Firm* — Ronald Terk Sia; Kevin C. Johnson; Steven W. Miller (57) ABSTRACT

An aqueous depilatory composition comprising a thioglycolate salt and a fluoride ion source.

14 Claims, 2 Drawing Sheets

(56) References Cited

U.S. PATENT DOCUMENTS

| | | | |
|---|---|---|---|
| 2004/0219118 A1* | 11/2004 | Slavtcheff et al. | 424/70.1 |
| 2006/0002878 A1 | 1/2006 | Acher et al. | |
| 2007/0269469 A1* | 11/2007 | Hall-Maxwell | 424/401 |
| 2012/0016381 A1 | 1/2012 | Hassan | |
| 2012/0059307 A1* | 3/2012 | Harris et al. | 604/20 |
| 2013/0042417 A1 | 2/2013 | Dring | |
| 2013/0042418 A1 | 2/2013 | Broyles | |
| 2013/0042419 A1 | 2/2013 | Broyles | |

FOREIGN PATENT DOCUMENTS

| | | |
|---|---|---|
| EP | 1402679 A2 | 3/2004 |
| EP | 1551250 A1 | 7/2005 |
| EP | 1604690 A1 | 12/2005 |
| EP | 2050433 A1 | 4/2009 |
| EP | 2286768 A2 | 2/2011 |
| EP | 2356918 A1 | 8/2011 |
| EP | 2356962 A1 | 8/2011 |
| EP | 2356963 A1 | 8/2011 |
| EP | 2356964 A1 | 8/2011 |
| EP | 2356965 A1 | 8/2011 |
| EP | 2356966 A1 | 8/2011 |
| EP | 2356967 A1 | 8/2011 |
| EP | 2356968 A1 | 8/2011 |
| EP | 2368541 A1 | 9/2011 |
| EP | 2368542 A1 | 9/2011 |
| FR | 1287305 A | 3/1962 |
| FR | 2105039 A1 | 4/1972 |
| FR | 2626468 A1 | 8/1989 |
| FR | 2924928 A1 | 6/2009 |
| GB | 2391475 A | 2/2004 |
| JP | 62230711 A | 10/1987 |
| JP | 63073910 A | 4/1988 |
| JP | 2300112 A | 12/1990 |
| JP | 6135825 A | 5/1994 |
| JP | 6135826 A | 5/1994 |
| JP | 06192056 | 7/1994 |
| JP | 9103320 A | 4/1997 |
| JP | 11012123 A | 1/1999 |
| JP | 2002204716 A | 7/2002 |
| JP | 2003040751 A | 2/2003 |
| WO | 8906122 A1 | 7/1989 |
| WO | 9621419 A1 | 7/1996 |
| WO | 9825581 A1 | 6/1998 |
| WO | 02092049 A | 12/2002 |
| WO | 2004096164 A1 | 11/2004 |
| WO | 2007046097 A2 | 4/2007 |
| WO | 2007119227 A2 | 10/2007 |
| WO | 2009002049 | 12/2008 |
| WO | 2009083836 A2 | 7/2009 |
| WO | 2009090362 A1 | 7/2009 |
| WO | 2011103220 A1 | 8/2011 |
| WO | 2011103221 A1 | 8/2011 |
| WO | 2011103222 A1 | 8/2011 |
| WO | 2011103227 A1 | 8/2011 |
| WO | 2011103229 A1 | 8/2011 |
| WO | 2011103230 A2 | 8/2011 |
| WO | 2011103231 A1 | 8/2011 |
| WO | 2011103232 A1 | 8/2011 |
| WO | 2011103233 A1 | 8/2011 |
| WO | 2011103234 A1 | 8/2011 |
| WO | 2011103250 A1 | 8/2011 |
| WO | 2011103251 A1 | 8/2011 |
| WO | 2011103252 A1 | 8/2011 |
| WO | 2011103253 A1 | 8/2011 |
| WO | 2011119328 A1 | 9/2011 |
| WO | 2011119557 A2 | 9/2011 |
| WO | 2011119794 A2 | 9/2011 |

OTHER PUBLICATIONS

"Sensitive Hair Removal and Finishing Cream Set"; Record ID 1327122; Boots; 4 pages GNPD; MINTEL.

"Depilatory Cream"; Record ID 103645; Reckitt Benckiser; 2 pages GNPD; MINTEL.

"Soothing Hair Removal Face Cream"; Record ID 1327960; American International Industries; 5 pages GNPD; MINTEL.

European Search Report; App. No. 11180355.7-2108; Mailing Date Jan. 2, 2012; 5 pages.

European Search Report; App. No. 11180356.5-2108; Mailing Date Dec. 23, 2011; 7 pages.

European Search Report; App. No. 11180352.4-2108; Mailing Date Jan. 2, 2012; 8 pages.

International Search Report; PCT/US2012/051077; Mailing Date Jan. 22, 2013; 16 pages.

European Search Report; App. No. 11181559.3-2108; Mailing Date Jan. 2, 2012; 7 pages.

European Search Report; App. No. 11177832.01-2108; Mailing Date Feb. 22, 2012; 7 pages.

* cited by examiner

EFFECTIVE DEPILATORY ARTICLE

CROSS REFERENCE TO RELATED APPLICATION

This application claims the benefit of U.S. Provisional Application No. 61/524,360, filed 17 Aug. 2011.

FIELD OF THE INVENTION

The present invention relates to a chemically active aqueous depilatory composition.

BACKGROUND OF THE INVENTION

Depilatory compositions used to remove unwanted hair by chemical activity are known. Such compositions may comprise reducing agents to degrade keratin in the hair and thus weaken the hair strands. These compositions may take the form of creams, lotions and the like which may be applied to the unwanted hair in a variety of ways, such as with a spatula. The spatula or another suitable implement is then used to scrape off the weakened hair strands and complete the depilation process. This can be a messy and awkward procedure for the user of the depilatory cream or lotion. By disposing the depilatory composition on a substrate one may overcome or mitigate such disadvantages. Substrate-based depilatory products are known from JP63073910A, US2006002878, JP6135826A, JP11012123A and JP62230711A.

While addressing the handling problems of creams and lotions, substrate-based aqueous depilatory compositions typically provide a lower dosage of active ingredients to the unwanted hair than creams or lotions, thus reducing their efficacy versus a lotion or cream. Accordingly, there exists a need for a substrate-based depilatory product that provides an improved level of depilatory action.

SUMMARY OF THE INVENTION

According to a first aspect of the invention, the applicants have surprisingly found that an aqueous depilatory composition with enhanced efficacy can be provided when the composition comprises a source of fluoride ions. Preferably the composition is in physical contact with a substrate, thereby forming a coated area of the substrate and resulting in a depilatory article.

According to a second aspect of the invention, a cosmetic method of removing hair from the skin is provided, comprising the steps of: applying a depilatory article according to the first aspect of the invention to a surface of mammalian skin, preferably human skin, leaving said depilatory article in contact with the skin for a period of at least 1 minute, preferably 2 to 10 minutes, more preferably 2 to 8 minutes, removing said depilatory article from the surface of the skin, and preferably rubbing, scraping, rinsing or wiping the surface of the skin in the area to which the depilatory article was applied.

According to a third aspect of the invention, a depilatory kit is also provided, comprising: a depilatory article according to the first aspect of the invention, optionally at least one of a pre-treatment skin care composition, a post-treatment skin care composition and/or a tool to assist removal of hair and/or aqueous depilatory composition after use, and packaging for said depilatory kit.

DETAILED DESCRIPTION OF THE INVENTION

As used herein the term "colloid-forming" includes chemical species that are able to form stable, aqueous solid-in-liquid colloidal systems, including nano-colloidal systems.

As used herein, the term "buffering base" refers to a base capable of opposing pH changes by means of chemical or physical (solubility) processes and thereby limiting the pH to less than or equal to 13.

As used herein, the term "water impermeable" includes materials or objects through which water in its liquid state does not pass.

As used herein, the term "sodium silicate" refers to $Na_2SiO_3$, any other silicate comprising sodium as the only cation besides silicon, and any other silicate comprising sodium. The same definition applies correspondingly to any other silicate, for example "potassium silicate" refers to $K_2SiO_3$, any other silicate comprising potassium as the only cation besides silicon and any other silicate comprising potassium, "ammonium silicate" to $(NH_4)_2SiO_3$, any other silicate comprising ammonium as the only cation besides silicon and any other silicate comprising ammonium and "manganese silicate" to $Mn_2SiO_4$, any other silicate comprising manganese as the only cation besides silicon and any other silicate comprising manganese.

The aqueous depilatory composition comprises at least one thioglycolate salt acting as a hair removal agent when the aqueous depilatory composition is applied to unwanted hair. Preferably, the aqueous depilatory composition comprises sodium, potassium, magnesium, calcium, beryllium, strontium, zinc, monoethanolamine, ammonium, tetralkylammonium, imidazolium, pyridinium, phosphonium or glyceryl thioglycolate salts, or mixtures thereof, which may include dianion forms of thioglycolate. More preferably, the aqueous depilatory composition comprises at least one of sodium, potassium, magnesium or calcium thioglycolate, or mixtures thereof. Even more preferably the aqueous depilatory composition comprises potassium or calcium thioglycolate, or mixtures thereof. In a preferred embodiment, the concentration of the conjugate acid of the thioglycolate salt is from 0.5% to 12.0%, more preferably from 0.8% to 8.0% and even more preferably from 1.0% to 6.0% by weight of the aqueous depilatory composition.

The depilatory composition comprises at least one efficacy enhancer selected from a fluoride ion source. Without wishing to be bound by theory, the applicants believe that the fluoride ions possess an anionic surface charge that enhances the dissociation of the thioglycolate salt via an attractive force imposed upon the cation in said thioglycolate salt. This increases the amount of conjugate acid formed from the thioglycolate salt and therefore increases the effectiveness of the aqueous depilatory composition. Additionally, any monovalent cations such as those present in the fluoride ion source, or derived from monovalent cation containing salts, are able to displace the cation of the thioglycolate salt and further enhance dissociation of said thioglycolate salt without leading to the large pH increases associated with poor safety characteristics among compositions of the prior art. Accordingly, the presence of some monovalent metal cations in the aqueous depilatory compositions is acceptable.

Depilatory compositions of the present invention may comprise a substrate, thus forming a depilatory article, to facilitate application of the aqueous depilatory composition to keratinous tissue and prevent a messy usage experience.

The substrate may be water permeable or water impermeable. The substrate may comprise any suitable material such as fibrous materials, papers, fabrics, non-wovens, plastics, amorphous solids, crystalline solids, foils, rubbers, latex, thermoplastic elastomers, cellular foams (open and closed cell), composites, and mixtures thereof. Preferably, the substrate is water impermeable. Using a substrate prevents water loss from the aqueous depilatory composition while the aqueous depilatory composition is in contact with the keratinous tissue and thus prevents the aqueous depilatory composition from drying out. Water loss from the aqueous depilatory composition lowers the water concentration, thus increasing the concentration of active ingredients and bases present. This could result in irritation to the skin, which applicants wish to avoid.

Depilatory articles of the present invention comprise an aqueous depilatory composition in contact with a surface of the substrate, forming a coated region of the substrate. The depilatory composition may be disposed on one surface of the substrate, that surface being a depilatory surface of the substrate. The aqueous depilatory composition should be suitable for being placed in contact with a user's skin (and unwanted hair). The fluoride ions aid to counteract the lowered efficacy upon making an acceptable substrate-based depilatory product.

Suitable fluoride ion sources include sodium fluoride, potassium fluoride, lithium fluoride, ammonium fluoride, tetrabutylammonium fluoride, tetraethylammonium fluoride, tetramethylammonium fluoride, imidazolium fluoride and mixtures thereof; preferably sodium fluoride, potassium fluoride, ammonium fluoride, tetrabutylammonium fluoride, tetraethylammonium fluoride, tetramethylammonium fluoride and mixtures thereof and even more preferably sodium fluoride, potassium fluoride, tetraethylammonium fluoride, tetramethylammonium fluoride and mixtures thereof. Without wishing to be bound be theory, the applicants believe that this particular selection of the fluoride ion source provides improved stability. In a preferred embodiment the source of fluoride ions contains a monovalent cation and even more preferably a monvalent metal cation.

In a preferred embodiment, the aqueous depilatory composition comprises from 0.05% to 8.0%, preferably from 0.05% to 5.0%, more preferably from 0.2% to 3.0% and even more preferably from 0.4% to 2% of a fluoride ion source by weight of the aqueous depilatory composition.

In situ, the fluoride comprised within the aqueous depilatory composition forms salts, which hydrates and tends to remove water from the composition. Since the salt may be colloidal, the colloidal solids may provide surfaces for evaporation and this evaporation, in turn, may be enhanced at the surface of the coated region intended to be placed in contact with the skin, which otherwise is a surface that may be open to the atmosphere. As indicated above, evaporation or other loss of water from the aqueous depilatory composition leads to a pH change that may lead to skin irritation which it is desirable to avoid. Applicants believe that, within certain dosage-per-unit-area ranges, the effects referred to above may be kept within acceptable limits. As a result, the fluoride ion source is preferably present in the aqueous depilatory composition in an amount per unit area of the coated region of from $2.05 \times 10^{-8}$ mol/cm$^2$ to $1.23 \times 10^{-4}$ mol/cm$^2$, preferably from $1.64 \times 10^{-7}$ mol/cm$^2$ to $3.69 \times 10^{-5}$ mol/cm$^2$ and more preferably from $4.92 \times 10^{-7}$ mol/cm$^2$ to $8.20 \times 10^{-6}$ mol/cm$^2$.

The aqueous depilatory composition may also comprise a silicate, preferably a water-soluble or colloid-forming silicate, believed to function in the same manner as the fluoride ion source. The aqueous depilatory composition may comprise at least one silicate selected from lithium silicates, sodium silicates (including disodium metasilicate pentahydrate and disodium metasilicate nanohydrate), potassium silicates, calcium silicates, ammonium silicates, manganese silicates, imidazolium silicates, synthetic and natural silicates (clays) or mixtures thereof. More preferably, the aqueous depilatory composition may comprise at least one water-soluble or colloid-forming silicate selected from synthetic clays, sodium silicates, potassium silicates, or mixtures thereof and even more preferably the aqueous depilatory composition may comprises a sodium silicate or mixtures of sodium silicates.

Suitable synthetic and natural silicates (clays) are available commercially as: Laponite® RDS; XLS and S etc. (available from RockWood Additives Limited); Wyoming Bentonite; Californian Hectorite; Jadeite; Enstaite and Rhodonite; Benonate® EW (available from Rheox Inc.); Bentolite® (available from Southern Clay Products Inc.) Optigel® (available from Süd Chemie Rheologicals).

The silicate is preferably present in the aqueous depilatory composition in an amount per unit area of the coated region of from $2.05 \times 10^{-8}$ mol/cm$^2$ to $1.23 \times 10^{-4}$ mol/cm$^2$, preferably from $1.64 \times 10^{-7}$ mol/cm$^2$ to $3.69 \times 10^{-5}$ mol/cm$^2$ and more preferably from $4.92 \times 10^{-7}$ mol/cm$^2$ to $8.20 \times 10^{-6}$ mol/cm$^2$.

The aqueous depilatory composition may also comprise a phosphate, sulphate or sulphite ion source, believed to function in the same manner as the fluoride ion source. Suitable phosphate ion sources include orthophosphates, pyrophosphates, tripolyphosphates, polyphosphates and mixtures thereof; preferably disodium phosphate dibasic, sodium pyrophosphate tetrabasic, potassium pyrophosphate tetrabasic, sodium phosphate tribasic dodecahydrate, tetrabutylammonium phosphate monobasic, ammonium phosphate dibasic, lithium phosphate, potassium phosphate and mixtures thereof and even more preferably disodium phosphate dibasic, sodium pyrophosphate tetrabasic, sodium phosphate tribasic dodecahydrate, potassium phosphate, potassium pyrophosphate tetrabasic and mixtures thereof. In a preferred embodiment the source of phosphate ions contains a monovalent cation and even more preferably a monvalent metal cation.

Suitable sulphate or sulphite ion sources include peroxomonosulphate, peroxodisulphate, pyrosulphate, metabisulphite and mixtures thereof; preferably sodium sulphate, sodium bisulphate, ammonium sulphate, potassium sulphate, sodium pyrosulphate, sodium metabisulphite, tetrabutylammonium sulphate, lithium sulphate and mixtures thereof and even more preferably sodium sulphate, sodium bisulphate, potassium bisulphate, sodium metabisulphite and mixtures thereof. In a preferred embodiment the source of sulphate or sulphite ions contain a monovalent cation and even more preferably a monvalent metal cation.

In a one embodiment, the aqueous depilatory composition comprises from 0.05% to 8.0%, preferably from 0.05% to 5.0%, more preferably from 0.2% to 3.0% and even more preferably from 0.4% to 2% of the phosphate, sulphate or sulphite ion source by weight of the aqueous depilatory composition.

In one embodiment, the aqueous depilatory composition comprises a monovalent cation, preferably a monovalent metal cation. Without wishing to be bound by theory, the applicants believe that the presence of monovalent metal cations increases the dissociation of thioglycolate salts. The monovalent cations such as those derived from monovalent cation containing salts are able to displace the cation of the thioglycolate salt and further enhance dissociation of said thioglycolate salt. This increases the amount of deprotonated thioglycolate formed from the thioglycolate salt and therefore increases the effectiveness of the aqueous depilatory composition. Sources of monovalent cations include potassium, sodium, lithium, ammonium, tetraalkyl ammonium and imidazolium salts, which may be a component of another ingredient, for example a thickening system or skin care active. Preferred sources of monovalent cations include potassium and sodium salts.

In order to further enhance the safety of the resulting product, it is advantageous to limit the amount of monovalent cations, preferably monovalent metal cations, to which the skin is exposed when the depilatory article is used, although a small quantity may improve the efficacy of the aqueous depilatory composition as discussed previously. Advantageously, the quantity of monovalent cations (or monovalent metal cations in the preferred embodiment above) per unit area of the aforementioned coated region is less than $5.10 \times 10^{-4}$ mol/cm$^2$, preferably less than $3 \times 10^{-4}$ mol/cm$^{-2}$, more preferably from $1 \times 10^{-9}$ mol/cm$^2$ to $1.5 \times 10^{-4}$ mol/cm$^2$, even more preferably from $2.50 \times 10^{-8}$ mol/cm$^2$ to $6.65 \times 10^{-5}$ mol/cm$^2$ and even more preferably still from $6 \times 10^{-7}$ mol/cm$^2$ to $4.5 \times 10^{-5}$ mol/cm$^2$. The selection of thioglycolate salt and optional ingredients including the base may be made considering the quantity of monovalent cations or monovalent metal cations achieved. The amount of monovalent ions present in the aqueous depilatory composition can be calculated from the ingredients or experimentally measured using standard elemental analysis techniques such as Inductively Coupled Plasma—Optical Emission Spectroscopy (ICP-OES), Atomic Absorption Spectroscopy (AAS) or Ion Chromatography (IC).

Limiting the quantity of monovalent ion present in the aqueous depilatory composition may prevent skin irritation but also limits the quantity of thioglycolate salt that may be present in a formula if monovalent ion containing thioglycolate salts or bases are used. Accordingly, in an advantageous embodiment, the aqueous depilatory composition comprises a divalent cation, preferably a divalent metal cation, and preferably wherein the thioglycolate salt, the buffering base (if present) or both comprises a divalent cation, or more preferably a divalent metal cation in order to enable the inclusion of additional depilatory active. In another preferred embodiment, the thioglycolate salt comprises a divalent metal cation. Applicants have established that thioglycolate salts comprising monovalent metal cations, such as potassium thioglycolate, are effective at removing hair from the skin, even at low doses, but may expose the skin tissue to harsh chemical conditions, resulting in irritation. On the other hand, thioglycolate salts comprising divalent metal cations, such as calcium thioglycolate, are relatively non-irritating to the skin.

In an aqueous depilatory composition comprising a mixture of monovalent and divalent ions, controlling the ratio of divalent ions to monovalent ions may also improve the safety characteristics of the depilatory articles of the present invention. Increasing the concentration of divalent ions relative to the concentration of monovalent ions increases the likelihood that any particular depilatory active species is associated with a divalent ion, rather than the more irritating monovalent ions. On the other hand, increasing the concentration of monovalent ions increases the effectiveness of the aqueous depilatory composition. Accordingly, in an alternative embodiment the ratio of the concentration of divalent ions to the concentration of monovalent ions present in the aqueous depilatory composition is advantageously in the range of from 400:1 to 0.02:1, preferably from 200:1 to 0.1:1, more preferably 60:1 to 0.3:1, even more preferably from 20:1 to 0.5:1, and even more preferably still from 15:1 to 1:1.

The pH of the aqueous depilatory composition may advantageously be in the range of from 6 to 13.8, preferably from greater than 7 to 13, more preferably from 9 to 12.9, even more preferably from 10 to 12.8, even more preferably still from 12 to 12.7 and yet more preferably from 12.3 to 12.6 to improve the efficacy of the active ingredient. The aqueous depilatory composition may, in a preferred embodiment, comprise at least one base to control the pH. Preferably, the aqueous depilatory composition comprises potassium hydroxide, sodium hydroxide, lithium hydroxide, calcium hydroxide, barium hydroxide, caesium hydroxide, sodium hydroxide, ammonium hydroxide, strontium hydroxide, rubidium hydroxide, magnesium hydroxide, zinc hydroxide, sodium carbonate, pyridine, ammonia, alkanolamides (including monoethanolamine, diethanolamine, triethanolamine), phosphates (including tetrasodium phosphate), arginine or mixtures thereof. More preferably, the aqueous depilatory composition comprises at least one buffering base, even more preferably the aqueous depilatory composition comprises calcium hydroxide, magnesium hydroxide, barium hydroxide, strontium hydroxide, zinc hydroxide, arginine or mixtures thereof. Still more preferably the aqueous depilatory composition comprises calcium hydroxide, magnesium hydroxide, zinc hydroxide, sodium hydroxide, potassium hydroxide or mixtures thereof. Even more preferably still, the aqueous depilatory composition comprises calcium hydroxide.

In a preferred embodiment, the base is present at a concentration of from 0.1% to 10.0%, more preferably from 0.5% to 8.0% and even more preferably from 1.0% to 5.0%, by weight of the aqueous depilatory composition.

The substrate preferably comprises at least one water impermeable material and is compatible with aqueous depilatory compositions. Examples of useful water impermeable materials include but are not limited to polypropylene (PP), polyethylene (PE, including HDPE and LLDPE), polyethylene terephthalate (PET), polyvinylchloride (PVC), polyamide (PA), polycarbonate, polyurethane, cellulose acetate, polychloropene; polysulfone, polytetrafluoroethylene (PTFE), polyvinyl acetate (PVA), polystyrene; polyphenylene oxide (PPO), acrylonitrile butadiene styrene (ABS), acrylic; acrylonitrile styrene acrylate (ASA), ethylene vinyl alcohol (EVA), natural rubber, latex, nylon, nitrile, silicone and thermo plastic elastomers (TPE). The substrate may comprise a single polymer or mixtures of polymers or copolymers. Preferably the substrate comprises a plastic sheet, more preferably a polyolefin, even more preferably a polyethylene and even more preferably still high density polyethylene.

In an advantageous embodiment, the aqueous depilatory composition is disposed upon the water impermeable material, preferably plastic sheet, more preferably polyolefin, even more preferably polyethylene and even more preferably still high density polyethylene. In this advantageous embodiment, there is preferably no layer of water permeable material between the aqueous depilatory composition and the water impermeable material. In a preferred embodiment, the water impermeable material forms a water impermeable layer.

The substrate preferably possesses a rigidity in the range of from 5.00 g/cm to 0.08 g/cm, more preferably from 3.00 g/cm to 0.08 g/cm, even more preferably from 1.80 g/cm to 0.10 g/cm, even more preferably still from 0.80 g/cm to 0.15 g/cm and yet more preferably from 0.60 g/cm to 0.25 g/cm. This rigidity of the substrate ensures that desirable handleability and conformability attributes of a depilatory article are achieved. In particular, the article collapsing under gravity or folding is avoided, which is especially undesirable if different areas of the aqueous depilatory composition are able to readily come into contact with each other, while maintaining the capability for the substrate to conform to the surface to which it is applied without folding or crinkling, in order to further improve depilatory efficiency. Accordingly, the substrate is readily conformable to the skin and unwanted hair without permanently deforming during use, as this may also result in problems for the user during application. In a preferred embodiment, the rigidity is substantially constant and does not change during the lifetime of a product.

Rigidity can be readily measured using the American Standard Test Method (ASTM) D2923-06, Method B (i.e. using a powder to reduce the effect of static electricity) on a Handle-O-Meter, model #211-300, available from Thwing-Albert Instrument Co. of Philadelphia, Pa. The rigidity is expressed as grams per centimetre of sample width. Samples were prepared as 10.16 cm (4 inch) by 10.16 cm (4 inch) test specimens with edges parallel to the machine direction and transverse direction for substrates with directionality. Three rigidity measurements were determined on the same side of fresh test specimens orientated in the same substrate direction. A further three rigidity measurements were taken on the same side of fresh test specimens oriented at 90° to the first orientation. These six measurements were repeated on the opposite side to the first six measurements, on fresh test samples. The 12 rigidity measurements were then averaged and reported to 0.01 g/cm.

The rigidity of a substrate is a function of substrate thickness and inherent modulus of elasticity. Different materials have different moduli of elasticity. Based upon the material or materials that the substrate comprises, a substrate thickness should be selected that enables the desired rigidity of the substrate to be achieved.

The substrate preferably has a thickness of from 80 µm to 12 µm, more preferably from 50 µm to 15 µm, even more preferably from 40 µm to 16 µm and even more preferably still from 30 µm to 17 µm.

Non-limiting examples of substrate material and thickness combinations for the substrate are:

| Substrate Material | Thickness [microns] | Rigidity [g/cm] |
|---|---|---|
| HDPE | 13 | 0.13 |
| HDPE | 18 | 0.33 |
| HDPE | 36 | 1.05 |
| LLDPE | 23 | 0.23 |
| PP | 18 | 0.46 |

[HDPE is a mixture of LBI 85% M6030 and Exxon Mobil 15% LD2001 manufactured on a Merritt-Davis casting line]
[LLDPE is Exxon Mobil 15% LD2001 manufactured on a Merritt-Davis casting line]
[PP is Basell PH835 manufactured on a Merritt-Davis casting line]

The substrate may comprise a textured or, alternatively, micro-structured surface on at least a portion of one side. Surface texturing or micro-structuring increases the effective surface area of the substrate and thus improves adherence of the aqueous depilatory composition to said substrate, facilitating an easy removal of the depilatory article by peeling it off the skin, or increases the grip of the surface, thus improving handleability. The textured structures may comprise dimples; lines or curvilinear embossments. A textured surface may be formed on the substrate by any appropriate technique, including embossment calendars and casting.

The substrate may be manufactured by any suitable method, including casting, injection moulding, co-injection moulding, over moulding, in-mold assembly, compression moulding, blow moulding, casting thermo or vacuum forming.

Achieving a desired dosage of aqueous depilatory composition to the surface of the skin is a further advantage of using a substrate-based product. However, if the substrate is able to stretch or tear, the layer of aqueous depilatory composition disposed upon it may be thinned, thickened or rupture in places, resulting in uneven and hence less desirable depilatory activity. In particular, low depilatory efficacy may result in areas treated with thinned or ruptured areas of the composition while higher depilatory efficacy and increased irritation may result in areas treated with thickened areas of the composition.

The potential problem of a substrate stretching may be avoided by selecting a substrate that does not permanently deform during use. This problem may also be avoided by selecting a substrate with a sufficiently high secant modulus such that it is less likely to stretch during normal use. Accordingly, in another preferred embodiment, the substrate has a secant modulus at 2% strain of greater than 689.5 bar (10,000 psi), more preferably greater than 1379.0 bar (20,000 psi), even more preferably greater than 2068.4 bar (30,000 psi) and even more preferably still greater than 2757.9 bar (40,000 psi) in order to achieve uniform application of the aqueous depilatory composition to the surface of the body during usage. Without wishing to be bound by theory, applicants believe that using a substrate with an excessively low secant modulus at 2% strain can deform and thus break apart the aqueous depilatory composition disposed on the substrate, leading to uneven depilatory action and increased risk of irritation. The secant modulus at 2% strain may be measured readily using the American Standard Test Method (ASTM)) 'Standard Test Method for Tensile Properties of Thin Plastic Sheeting D882-09' conducted on an MTS Insightl Tensile Tester available from MTS Systems Co, Eden Prairie, Minn., USA. This method may also be applied to non-plastic materials and is designed for use on sheets with a thickness of less than 1 mm.

The potential problem of a substrate tearing may be avoided by selecting a substrate that does not fail during usage. This problem may also be avoided by selecting a substrate with a sufficiently high nominal tensile strength such that it is less likely to tear during normal use. Accordingly, in another preferred embodiment, the substrate has a nominal tensile strength of at least 5 MPa more preferably at least 10 MPa even more preferably at least 15 MPa and even more preferably still at least 18 MPa in order to achieve uniform application of the aqueous depilatory composition to the surface of the body during usage. Without wishing to be bound by theory, applicants believe that using a substrate with an excessively low nominal tensile strength can fail during usage and thus break apart the aqueous depilatory composition disposed on the substrate, leading to uneven depilatory action and increased risk of irritation. The nominal tensile strength may be measured readily using the American Standard Test Method (ASTM) 'Standard Test Method for Tensile Properties of Thin Plastic Sheeting D882-09' conducted on an MTS Insightl Tensile Tester available from MTS Systems Co, Eden Prairie, Minn., USA. This method may also be applied to non-plastic materials and is designed for use on sheets with a thickness of less than 1 mm.

A layer of aqueous depilatory composition can be applied to the substrate through any known technique of applying viscous fluids to substrates, including, for example, extrusion, casting (e.g., reverse roll, knife-over roll, slot die, Gravure roll), spraying, knife blade coating, and zone coating. Such techniques may be modified to alter the quantity of aqueous depilatory composition disposed on the substrate. For example, the speed at which the substrate travels through an extrusion process determines the quantity of aqueous depilatory composition disposed upon said substrate. The area of aqueous depilatory composition may cover the entire surface of the substrate of a portion thereof. Advantageously, the aqueous depilatory composition covers less than the entire surface of the substrate to facilitate handling. The substrate may comprise at least one region with two orthogonal dimensions each of a length greater than 1 cm, preferably greater than 1.5 cm and more preferably greater than 2 cm upon which no aqueous depilatory composition is disposed.

Preferably, the aqueous depilatory composition is disposed upon the substrate in an amount per unit area of 0.300 g/cm$^2$ to 0.001 g/cm$^2$, more preferably from 0.015 g/cm$^2$ to 0.003 g/cm$^2$, even more preferably from 0.080 g/cm$^2$ to 0.005 g/cm$^2$ and even more preferably still from 0.05 g/cm$^2$ to 0.005 g/cm$^2$, wherein the unit area refers to the coated region of the substrate and not including any uncoated surface of the substrate. Additionally, the area used to calculate the amount of aqueous depilatory composition disposed upon the substrate is calculated ignores any surface texturing or micro-structuring. Alternatively, the mean thickness of the aqueous depilatory composition is preferably from 0.01 mm to 3 mm, more preferably 0.1 mm to 1.5 mm, even more preferably from 0.05 mm to 0.8 mm, and even more preferably still from 0.05 mm to 0.5 mm.

The concentration of water in the aqueous depilatory composition is preferably at least 40%, more preferably from 50% to 98%, even more preferably from 60% to 95% and even more preferably still from 70% to 90%, by weight of the aqueous depilatory composition. This high water level helps to improve the overall skin mildness of the aqueous depilatory composition by being dilute, and to keep the system more robust to pH changes, which may result in skin irritation.

The aqueous depilatory composition may optionally comprise a thickening agent. A representative but not exhaustive list can be found in "The Encyclopedia of Polymers and Thickeners for Cosmetics" compiled and edited by Robert Y. Lochhead, PhD and William R. Fron, Department of Polymer Science, University of Southern Mississippi. Exemplary classes of thickening agents include gums, carbomers, polymers and copolymers of acrylic acid, associated thickeners, layered silicates/clays and natural polymers (including polysaccharides). One or more thickening agents may be included in the aqueous depilatory composition. It may be desirable to utilize gel network structures or oil-in-water emulsions to thicken the aqueous depilatory compositions. Suitable materials for preparing the gel network structures or oil-in-water emulsions are well represented in the art and include fatty materials such as fatty alcohols (for example cetyl alcohol and stearyl alcohol) alone or used in conjunction with non-polar oils such as paraffin or mineral oils. An appropriate emulsifier may also be used to form and stabilize the bilayer structure characteristic of gel network structures or to form and stabilize an oil-in-water emulsion. The thickening agent may be present at a level of from about 0.01% to about 20%, preferably from about 0.1% to about 10%, more preferably from about 0.3% to about 5%, and even more preferably from about 0.5% to about 4%, by weight of the aqueous depilatory composition.

Advantageously, the thickening agent comprises carrageenan. The carrageenan is preferably present in an amount of from 0.1% to 10%, more preferably from 0.5% to 8%, even more preferably from 1% to 5% and even more preferably still from 2% to 4% by weight of the aqueous depilatory composition. The carrageenan may be iota, kappa or lambda carrageenan, and in a preferred embodiment is iota carrageenan. Without wishing to be bound by theory, the applicants believe that a depilatory composition comprising carrageenan has both an affinity to the surface of the skin, providing an effect analogous to a frictional resistance opposing spreading of the composition and cohesive forces that further prevent spreading and additionally prevent rupturing of the composition.

The rheological properties of the aqueous depilatory composition may also lead to improved performance in use. In particular, the yield point describes the resistance of the aqueous depilatory composition to deformation under environmental stress. If the yield point is too high, then the aqueous depilatory composition may not deform sufficiently, with hair fibres unable to enter the aqueous depilatory composition effectively upon application, resulting in less desirable depilatory effectiveness. If the yield point is too low, however, then the aqueous depilatory composition may flow during storage, transport or use and is not cleanly removed from the skin upon removal of the depilatory article, thus requiring the inconvenience of additional wiping and risking irritation to the user. Accordingly, the phase angle of the aqueous depilatory composition preferably has a yield point from 10 Pa to 2000 Pa, more preferably from 30 Pa to 1200 Pa, even more preferably from 45 Pa to 500 Pa and even more preferably still from 60 Pa to 300 Pa, when measured via a stress controlled amplitude sweep at a frequency of 1 Hz and a temperature of 25° C. The yield point described is defined as the 5% decrease in magnitude of the elastic modulus G' linear viscoelastic plateau value as measured on a TA1000 Rheometer, available from TA Instruments of New Castle, Del., USA. The rheological properties of the aqueous depilatory composition may be altered by changing the concentration or identity of the thickening system and the water content of the aqueous depilatory composition.

Advantageously, the aqueous depilatory composition displays an elastic modulus G' which exceeds its viscous modulus G" at all frequencies below 60 rad/s, preferably below 20 rad/s, more preferably below 10 rad/s and even more preferably below 1 rad/s; when measured via a strain controlled frequency sweep; at a strain of 1% and a temperature of 25° C. The elastic modulus of the aqueous depilatory composition exceeds its viscous modulus at a low frequency of applied stress. This indicates that the aqueous depilatory composition is behaving in a solid-like manner at rest and is of particular benefit when the aqueous depilatory composition is interposed between two substrates, for example a substrate and a protective release layer.

In another preferred embodiment, the aqueous depilatory composition displays a high degree of shear thinning behaviour enabling the effective coating of target hairs during application and improve depilatory efficacy. Accordingly, at a low shear rate of 0.1 s$^{-1}$, the dynamic viscosity of the aqueous depilatory composition is preferably 1000 Pa·s to 10000 Pa·s measured at a temperature of 25° C., whereas at a high shear rate of 1000 s$^{-1}$, the dynamic viscosity of the aqueous depilatory composition is preferably 0.1 Pa·s to 1 Pa·s, measured at a temperature of 25° C.

The aqueous depilatory composition may also include other skin care ingredients such as conditioning agents selected from the group consisting of humectants, moisturizers, or skin conditioners (including mineral oil, almond oil, chamomile oil, jojoba oil, avocado oil, shea butter, niacinamide and glycerine), skin rejuvenation compositions (for example targeted for fine lines, wrinkles and uneven skin tone including retinoids), cosmetic compositions, anti-inflammatory agents (including corticosteroids), anti-oxidants (including flavonoids), radical scavengers, sunscreen agents, skin cooling or warming agents and the like. The aqueous depilatory composition may comprise one or more skin care ingredients present in an amount of from about 0.001% to about 10%, more preferably from about 0.01% to about 7%, and even more preferably from about 0.025% to about 5%, by weight of the aqueous depilatory composition.

An accelerant may be employed in the aqueous depilatory composition. This optional component accelerates the rate of depilatory action of the depilatory agent. Suitable accelerants include, but are not limited to, urea, thiourea, dimethyl isosorbide, arginine salts, ethoxydiglycol, propylene glycol and methylpropyldiol. The accelerant may be present in a concentration range of from 0.5% to 10%, more preferably from 2% to 8% and even more preferably from 2% to 5% by weight of the aqueous depilatory composition.

The aqueous depilatory composition may further comprise components known, conventionally used, or otherwise effective for use in hair removal compositions particularly dyes; pigments (including ultra marines and talc); anionic, cationic, non-ionic and/or amphoteric or zwitterionic surfactants, polymers (including hydrophobically modified polymers); dispersing agents; solvents; lubricants; fragrances; preservatives; chelants; proteins and derivatives thereof; plant materials (e.g. aloe, chamomile and henna extracts); silicones (volatile or non-volatile, modified or non-modified); film-forming agents; film forming promoters and mixtures thereof.

Depilatory articles of the present invention may take any form suitable for applying to keratinous tissue. The size and shape of the depilatory article may take any form suitable for application to the body area from which hair is to be removed. The depilatory article will preferably relate to the body area or zone from which hair is to be removed, especially the face (including the jaw, chin and upper lip regions of the face), underarm and bikini areas. Preferably, the depilatory article takes the form of a mask (configured for the face) or a strip/patch (configured for general use). In another preferred embodiment, the substrate of the depilatory article is substantially planar.

The coated region preferably comprises an upper-lip portion adapted to be placed above a human mouth, and a first return portion projecting from the upper lip portion and adapted to be placed contiguously with the outer extremity of the vermilion lip in a first corner of the mouth. The return portion has a length along its greatest dimension of at least 0.2 cm, preferably from 0.5 cm to 5 cm, more preferably from 0.75 cm to 4 cm, even more preferably from 1 cm to 3 cm. Applicants have found that this configuration enables the user to remove unwanted hair from the skin immediately surrounding the corner of the mouth while lowering the risk of depilatory composition contacting the vermillion lip, where it may cause irritation. In an alternative embodiment, the coated region further comprises a second return portion projecting from the upper lip portion and adapted to be placed contiguously with the outer extremity of the vermillion lip in a second corner of the mouth.

Advantageously, the upper lip portion has a length along its greatest dimension of at least 0.2 cm, preferably from 0.5 cm to 15 cm, more preferably from 1 cm to 12 cm, even more preferably from 2 cm to 10 cm and even more preferably still from 3 cm to 8 cm. This dimension enables the upper lip portion to cover a desirable length of the upper lip and thus achieve the desired depilatory action. In a preferred embodiment, the upper lip portion is adapted to be placed to be at least partially contiguously with the upper border of the upper vermilion lip, to enable depilatory action to be achieved on the skin immediately surrounding the upper vermilion lip while lowering the risk of depilatory composition contacting the upper vermilion lip, where it may cause irritation.

In another preferred embodiment, the coated region comprises a lower lip portion adapted to be placed below a human mouth, preferably wherein the lower lip portion is adapted to be placed to be least partially contiguously with the lower border of the lower vermilion lip to enable depilatory action to be achieved on the skin immediately surrounding the lower vermilion lip while lowering the risk of depilatory composition contacting the lower vermilion lip, where it may cause irritation.

Depilatory articles of the present invention may comprise at least two finger-tabs being substantially free of aqueous depilatory composition and positioned on substantially opposing sides of the coated region. These finger tabs enable a user to apply tension to the coated region of the substrate. Surprisingly, applicants have found that applying tension across the coated region of the depilatory article creates an effect of temporarily causing the coated region to exhibit an apparent increased rigidity, enabling the user to accurately position the coated region, and hence aqueous depilatory composition on to the desired region of the body. Tensioning the coated region may be achieved in a number of ways, non-limiting examples of which include holding the depilatory article either side of the coated region, for example with the hands or a tool, so as to apply tension between the areas being held. Alternatively, depilatory articles of the present invention may comprise at least one finger-tab being substantially free of aqueous depilatory composition and positioned to allow the weight of the article to tension the coated region when being held by the finger-tab.

In a preferred embodiment, at least one finger tab extends from the perimeter of the coated region by a minimum of 1 cm, preferably from 1.5 cm to 5 cm, more preferably from 2 cm to 4 cm and even more preferably from 2.5 cm to 3.5 cm. In another preferred embodiment, both finger-tabs extend from the perimeter of the coated region by a minimum of 1 cm, preferably from 1.5 cm to 5 cm, more preferably from 2 cm to 4 cm and even more preferably from 2.5 cm to 3.5 cm, in order to aid handling of the depilatory article.

Depilatory articles of the present invention may comprise a protective release layer removably attached to the aqueous depilatory composition, preferably on a surface of the aqueous depilatory composition substantially opposing that which is in contact with the substrate. The protective release layer may comprise materials including polymer resins such as a polyolefins e.g. polypropylene (including stratified biaxially oriented polypropylene (SBOPP)), polyethylene (including LDPE; LLDPE; HDPE; Metallocene) or polyethylene terephthalate. Alternative materials which may be used include polyvinylchloride, polyamide, acetyl, acrylonitrile butadiene styrene, acrylic, acrylonitrile styrene acrylate, ethylene vinyl alcohol, ethylene vinyl acetate, nylon, Latex, natural or synthetic rubbers, polycarbonate, polystyrene, silicone or thermo plastic elastomer, thermo plastic vulcanate or copolymers of said materials. Where appropriate the protective release layer may comprise one or more laminations, combinations of multiple layers and/or indications (which may include instructions and illustrations) relating to at least one aspect of the usage of the depilatory article. In an advantageous the protective release layer may comprise a coating of a non-stick material. Exemplary non-stick coatings include wax, silicone, fluoropolymers such as TEFLON®, and fluorosilicones. In a preferred embodiment, the protective release layer covers at least the entire aforementioned coated region of the substrate. In another preferred embodiment the protective release layer is water impermeable. In a further preferred embodiment, the protective release layer has a mean thickness of at least 85 microns, more preferably from 85 microns to 130 microns, even more preferably from 90 microns to 120 microns. In yet another preferred embodiment, the protective release layer extends beyond the coated region of the substrate to provide a removal tab.

In a preferred embodiment, the depilatory articles of the present invention are packaged to prevent water loss and/or oxygen permeation. Alternatively, the depilatory articles of the present invention are packaged in water impermeable packaging. Examples of suitable packaging materials include films of EVOH; PP; PE; nylon; or mixtures thereof. More preferably, the packaging comprises an inert gas and even more preferably the inert gas comprises at least one of nitrogen, argon or carbon dioxide. Alternatively, the packaging comprises a partial vacuum.

A second aspect being a method of removing hair from the skin is also provided by the present invention, comprising the steps of:
 (a) applying a depilatory article according to the present invention to the surface of the skin, preferably mammalian and more preferably human skin;
 (b) leaving said depilatory article in contact with the skin for a period of at least 1 minute, preferably 2 to 10 minutes, more preferably 2 to 8 minutes;
 (c) removing said depilatory article from the surface of the skin; and
 (d) preferably rubbing, scraping, rinsing or wiping the surface of the skin in the area to which the depilatory article was applied.

Advantageously, the method of removing hair from the skin further comprises the step of tensioning the coated region of the depilatory article prior to applying it to the skin.

The same means used to apply tension to the coated region may be used to ensure that the depilatory article is applied to the surface of the body such that the coated region is applied under tension to the unwanted hair in order to maintain the improved handling characteristics described above. In a preferred embodiment, the tension is kept substantially constant during application of the depilatory article. The flexible nature of the substrate allows the substrate to conform to the surface of the body to offer improved contact between the aqueous depilatory composition and the unwanted hair. In a preferred embodiment, the tension may be at least partially, more preferably substantially completely released from the coated region after applying the depilatory article to the skin in order to improve the conformability of the depilatory article.

A third aspect being a depilatory kit is also provided by the present invention, which comprises at least one depilatory article of the present invention, packaging for said depilatory article(s), and at least one of a third component selected from:
 a) a pre-treatment skin care composition which may comprise ingredients to promote skin conditioning (e.g. emollients), hair hydration or provide a skin barrier (e.g. hydrophobic materials) and intended for use prior to applying the depilatory article;
 b) a post-treatment skin care composition which may comprise ingredients to promote skin conditioning; moisturizers, skin rejuvenation compositions (targeted for fine lines, wrinkles and uneven skin tone, for example), cosmetic compositions (e.g., foundation, rouge), sunscreens and the like as described herein above;
 c) a tool to assist in the removal of hair and/or aqueous depilatory composition from the skin; or
 d) indications (which may include instructions and/or illustrations) relating to at least one aspect of usage of the depilatory article or another component of the kit.

The complementary post treatment skin care compositions may be leave-on or rinse-off compositions. The skin care compositions may also be designed to immediately follow application of the hair removal products. For example, a finishing composition may be applied to the same skin area to combat lingering odour and irritation caused by residual depilatory agent. The finishing composition may comprise a metal oxide (e.g., zinc oxide, aluminum oxide, and magnesium oxide) that is capable of complexing with any remaining depilatory agent remaining on the targeted skin area to reduce continued odour and subsequent skin irritation.

Figure 1:
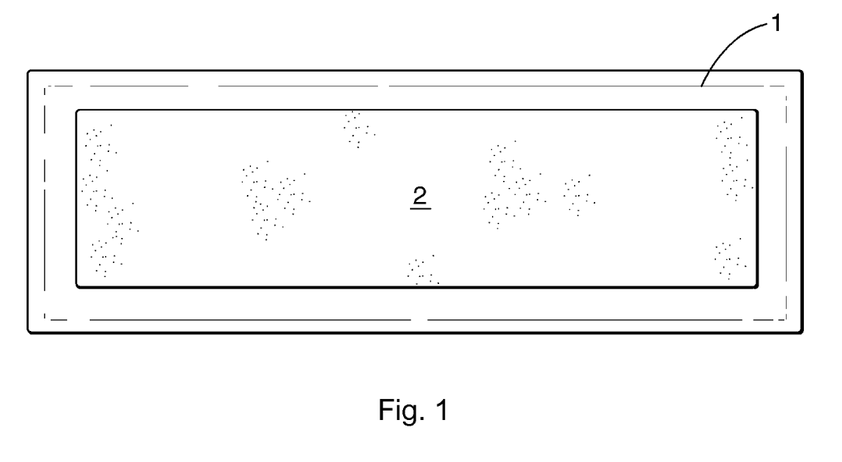
FIG. 1. is a plan view of a depilatory article.
Figure 2:
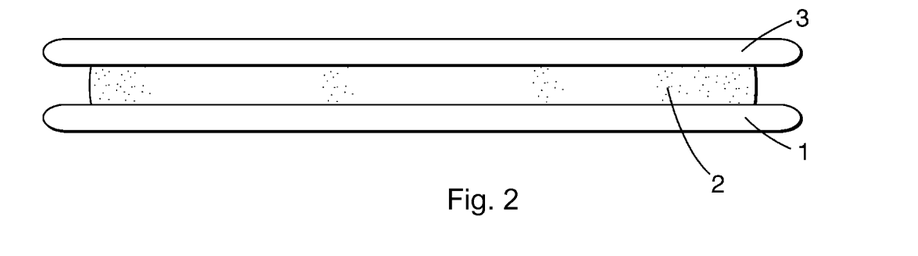
FIG. 2. is a side view of a depilatory article.
Figure 3:
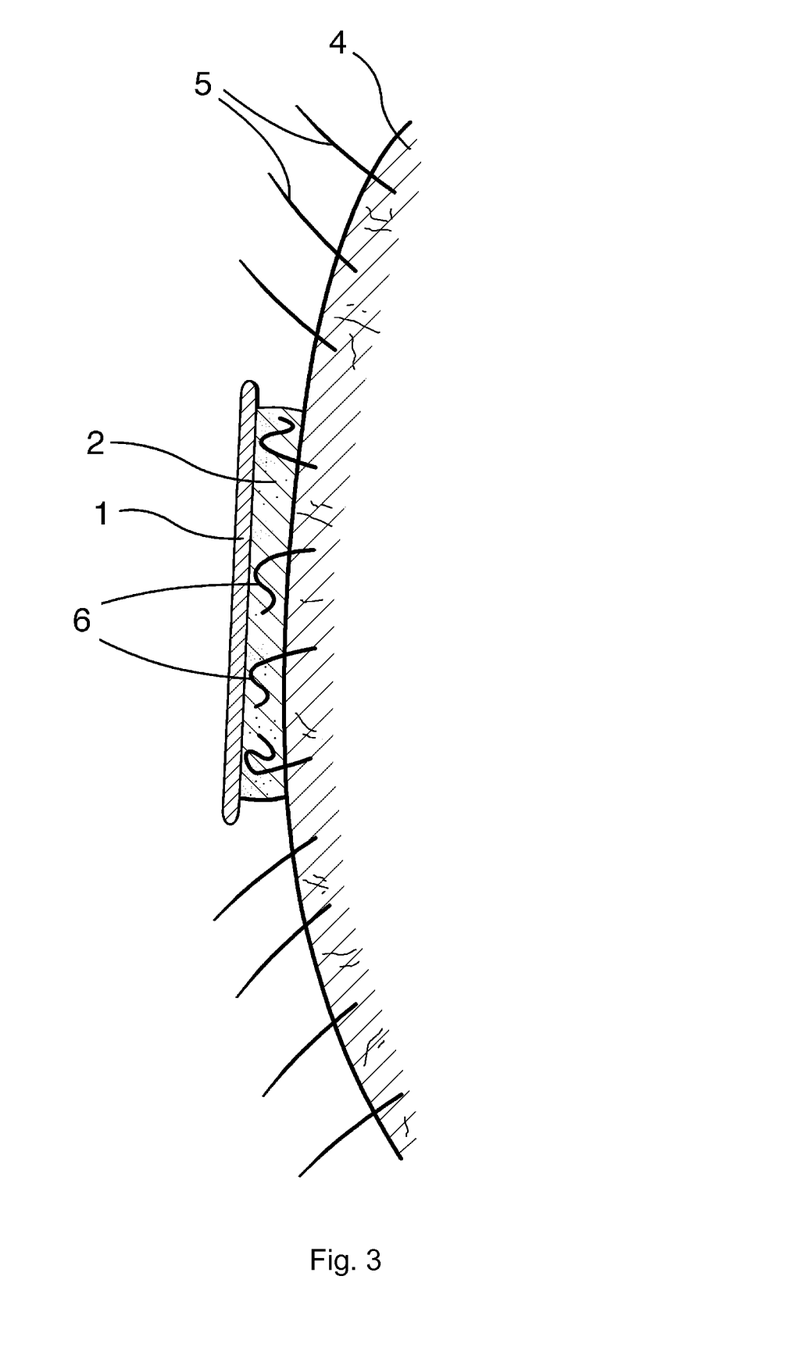
FIG. 3. is a side view of a depilatory article applied to keratinous tissue.

Reference is made to the figures, which disclose a non-limiting embodiment of the invention. FIG. 1 depicts a plan view of a depilatory article of the present invention, comprising a substrate (1) and an aqueous depilatory composition (2). FIG. 2 depicts a side view of a depilatory article of the present invention, further comprising a protective release layer (3). FIG. 3 depicts a side view of a depilatory article of the present invention in use, i.e. applied to keratinous tissue which comprises the skin (4), hair strands (5) outside the aqueous depilatory composition (2) and hair strands (6) within the aqueous depilatory composition (2).

The following examples further describe and demonstrate one embodiment within the scope of the present invention. The examples are given solely for the purpose of illustration and are not to be construed as a limitation of the present invention, as many variations thereof are possible.

EXAMPLE 1

Diastron Tensile Testing

The Diastron Tensile Tester is an automated tool that measures mechanical properties of single hair fibres (cross sectional area, elastic, plateau, yield and breakage parameters), which can be used to determine the hair removal efficacy of depilatory products. The measurement of the average cross-sectional area of each hair fibre enables the tensile data to be normalized.

The Diastron Tensile Tester is available from Diastron Ltd in the UK, and consists of a Fibre Loading System, a FDAS765 Fibre Dimensional Analysis System and a MTT685 Miniature Tensile Tester.

Preparation of Fibres:

Chinese hair available from Kurling International (Chinese Hair 90 µm in diameter) was used to determine the hair removal efficacy of aqueous depilatory compositions with different efficacy enhancers. The hair strands were cut and removed from the hair switch and individually threaded through two brass ferrules ensuring a few centimetres of hair is left at either end. The hair fibre with the two brass ferrules was loaded onto a mounting block (in the same direction—root to tip) and pressure applied to the two brass ferrules to securely hold the fibres in accordance with the manufacturer's instructions.

In total, 100 individual fibres were tested on the Diastron Tensile Tester in one run (34 untreated control fibres; 33 with the control depilatory composition without an enhancer and 33 fibres with the aqueous depilatory composition with an enhancer). The untreated control fibres were loaded onto the 100 fibre rotary cassette with the root end of the hair fibre placed on the inside of the rotary cassette and each fibre labeled for identification.

The individual fibres to be treated with the control depilatory composition (with no enhancer) were placed in parallel with a transparent plastic treatment box positioned on top of the hair fibres to ensure accurate dosing. The plastic treatment box was 11.0 cm in length, 2.7 cm in width and 3.0 cm in depth. A maximum of four individual hair fibres were treated at any one time.

The plastics box was filled to a depth of 1.0 cm with the control depilatory composition (with no enhancer) and smoothed over evenly with spatula to ensure every hair fibre was coated. The control depilatory composition was left on the fibres for 5 minutes and then the plastic box was removed and the fibres very carefully placed in deionised water (100 ml) for 1 minute. The fibres were then removed and placed in fresh deionised water (100 ml) for 2 minutes and then yet again removed and placed in deionised water for 2 minutes. The pH of the deionised water was measured with pH paper (Universal pH Paper available from Whatman). If the pH was neutral (pH 7) the fibres were then loaded in the 100 fibre rotary cassettes with the root end of the hair fibre placed on the inside of the rotary cassette and each fibre labeled for identification. If the pH was >7 the last rinsing step was repeated until the pH was neutral.

This process was repeated until all 34 fibres had been treated with the control depilatory composition (with no enhancer). Then the process was repeated for the aqueous depilatory composition inventive example with the enhancer to be evaluated and labeled appropriately on the rotary cassette. The fibres were allowed to dry on the carousel in a controlled environment (25° C. and 50% RH) for 24 hours prior to measurement on the Diastron Tensile Tester.

Diastron Tensile Tester Method

The Diastron Tensile Tester was operated according to the manufacturer's instructions and a stress-strain curve obtained. For details of the stress-strain curves and the tensile method see Clarence R Robbins, Chemical & Physical Behavior of Human Hair, 3rd Ed, Springer-Verlag, 1994, p 300. The cross sectional areas were measured on all the dry individual fibres first and then each individual hair fibre was tensile tested after being completely saturated with deionised water. The following settings were used: Percentage extension=100%, Rate of Extension=20mm/min, Break detection Limit=-10, Maximum force=200 gmf. The deionised water auto-dosing system was enabled to ensure all the individual hair fibres were soaked in deionised water before tensile testing (tensile measurements are made at 100% humidity). The syringe supplying the deionised water was refilled if necessary.

The data output was first converted such that the x-axis of the stress/strain graph was reported in microns and the y-axis was reported in grams force (gmf). The UNWIN software (available form Diastron Ltd UK) was used to determine 3 phase data points of the stress/strain curves (including the Break Stress and Break Extension) for each individual hair fibre.

The break ratio was calculated for all the individual hair fibres as follows:

$$BreakRatio = \frac{BreakStress(gmf/\mu m^2)}{BreakExtension(\mu m)}$$

The average Break Ratio was calculated for the untreated control fibres and used to calculate the % Break Ratio Reduction for each individual hair fibre treated.

$$\% BreakRatio\ Reduction = \frac{BreakRatio(UntreatedControl) - BreakRatio(Option)}{Break\ Ratio(UntreatedControl)}$$

The average % Break Ratio Reduction (% BRR) was calculated for each option and is a measure of how much the tensile properties of an individual hair fibre have been weakened by the treatment compared to an average untreated hair fibre. The difference between the % Break Ratio Reduction for the inventive examples and the comparative example (% $BRR_{inventive}$–% $BRR_{comparative}$) was reported. The greater the difference, the more the hair has been weakened by the inventive example (see Table 1) and thus the more efficacious is the hair removal power of the aqueous depilatory composition.

TABLE 1

Diastron Tensile Testing

| Ingredients % w/w | Comparative Example | Inventive Example 1 |
|---|---|---|
| Deionised water | 85.00 | 87.53 |
| Carrageenan CI-123[1] | 3.5 | 2.60 |
| Calcium Hydroxide[2] | 3.25 | 3.25 |
| Calcium Thioglycolate Trihydrate[3] | 5.50 | 5.50 |
| Tetraethylammonium Fluoride[4] | — | 1.12 |
| Difference in % Break Ratio Reduction compared to comparative example (% $BRR_{Inventive}$ – % $BRR_{Comparative}$ | 0 | 14 |
| pH | 12.46 | 12.27 |

[1]Carrageenan CI-123 available from CPKelco
[2]Calcium Hydroxide Reag. Ph. Eur. puriss. p.a. available from Sigma-Aldrich Co.
[3]Calcium Thioglycolate Trihydrate 99.8% available from BRUNO BOCK Chemische Fabrik GmbH & Co.
[4]Tetraethylammonium Fluoride (CAS# 665-46-3) available from Sigma-Aldrich Co A 400 ml speed mixer plastic pot was sanitized and deionised water weighed in directly. The calcium hydroxide was added with mixing followed by the slow addition of the efficacy enhancer with mixing (for the inventive examples). The carrageenan or alternative thickener was then slowly added to the batch with mixing to ensure hydration, adjusting mixing speeds and time as required. The calcium thioglycolate was then added with mixing, again adjusting mixing speeds and time as required. The batch was then milled using an IKA T50 (5,200) rpm for 2 minutes. The pH was measured and the batch stored in glass pots with no head space. The amount of carrageenan CI-123 or alternative thickener used was modified in the inventive examples and less than that used in the comparative example in order to achieve comparable rheological properties and remove this as a potential cause for different results.

Further inventive examples are shown in the table below.

TABLE 2

Further Inventive Examples

| Ingredients % w/w | Inventive Example 2 | Inventive Example 3 |
|---|---|---|
| DI water | 88.37 | 85.62 |
| Carrageenan CI-123 | 2.60 | N/A |
| Ultrathix P-100[1] | N/A | 3.5 |
| Calcium Hydroxide | 3.25 | 4.50 |
| Calcium Thioglycolate Trihydrate | 5.50 | 6.0 |
| Ammonium Fluoride[2] | 0.28 | N/A |
| Sodium Fluoride[3] | N/A | 0.38 |
| pH | 12.32 | 12.48 |

[1]Ultrathix P-100 available from International Specialty Products (ISP)
[2]Ammonium Fluoride (CAS 12125-01-8)) available from Sigma-Aldrich Co.
[3]Sodium Fluoride (CAS 7681-49-4) available from Sigma-Aldrich Co.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." All percentages used herein are by weight of the aqueous depilatory composition, unless otherwise specified.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An aqueous depilatory composition comprising:
    i. a thioglycolate salt; and
    ii. a fluoride ion source selected from the group consisting of sodium fluoride, potassium fluoride, lithium fluoride, ammonium fluoride, tetrabutylammonium fluoride, tetraethylammonium fluoride, tetramethylammonium fluoride, imidazolium fluoride and mixtures thereof.

2. A depilatory composition according to claim 1, wherein the aqueous depilatory composition comprises a base in a concentration range of from about 0.1% to about 10.0% by weight of the aqueous depilatory composition.

3. A depilatory composition according to claim 2, wherein the base comprises a divalent cation.

4. A depilatory composition according to claim 1, wherein the thioglycolate salt comprises a divalent cation and wherein the concentration of the conjugate acid of the thioglycolate salt is from about 0.5% to about 12.0% by weight of the aqueous depilatory composition.

5. A depilatory composition according to claim 1, wherein the aqueous depilatory composition comprises water in an amount of at least about 40% by weight of the aqueous depilatory composition.

6. A depilatory article comprising a substrate in physical contact with the aqueous depilatory composition of claim 1, thereby forming a coated area of the substrate.

7. A depilatory article according to claim 6, wherein the fluoride ion source is present in the aqueous depilatory composition in an amount per unit area of said coated region of the substrate of from about $2.05 \times 10^{-8}$ mol/cm$^2$ to about $1.23 \times 10^{-4}$ mol/cm$^2$.

8. A depilatory article according to claim 6, wherein the aqueous depilatory composition comprises monovalent cations in an amount per unit area of the coated region of the substrate of less than about $5.10 \times 10^{-4}$ mol/cm$^2$.

9. A depilatory article according to claim 6, wherein a protective release layer is removably attached to the aqueous depilatory composition.

10. A depilatory article according to claim 6 wherein the depilatory article is a mask, strip or patch.

11. A depilatory article according to claim 6, wherein the substrate is water impermeable.

12. A depilatory article according to claim 6, wherein the substrate possesses a rigidity in the range of from about 5.00 g/cm to about 0.08 g/cm.

13. A method of removing hair from the skin, comprising the steps of:
    (a) applying a depilatory article according to claim 6 to a surface of skin,
    (b) leaving said depilatory article in contact with the skin for a period of greater than 1 minute,
    (c) removing said depilatory article from the surface of the skin, and
    (d) rubbing, scraping, rinsing or wiping the surface of the skin in the area to which the depilatory article was applied.

14. A depilatory kit, comprising:
    (a) at least one depilatory article according to claim 6,
    (b) optionally, at least one of: a pre-treatment skin care composition, a post-treatment skin care composition or a tool to assist removal of hair and/or aqueous depilatory composition after use, and
    (c) packaging for said depilatory kit.

* * * * *